United States Patent
Scher et al.

(10) Patent No.: US 10,030,271 B2
(45) Date of Patent: Jul. 24, 2018

(54) GENE EXPRESSION PROFILE ASSOCIATED WITH PROSTATE CANCER

(71) Applicant: MEMORIAL SLOAN-KETTERING CANCER CENTER, New York, NY (US)

(72) Inventors: Howard Scher, Tenafly, NJ (US); Martin Fleisher, Glen Cove, NY (US); Daniel Danila, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

(21) Appl. No.: 14/422,125

(22) PCT Filed: Aug. 19, 2013

(86) PCT No.: PCT/US2013/055563
§ 371 (c)(1),
(2) Date: Feb. 17, 2015

(87) PCT Pub. No.: WO2014/028925
PCT Pub. Date: Feb. 20, 2014

(65) Prior Publication Data
US 2015/0191792 A1 Jul. 9, 2015

Related U.S. Application Data

(60) Provisional application No. 61/684,351, filed on Aug. 17, 2012.

(51) Int. Cl.
*C12Q 1/68* (2018.01)
*C12Q 1/6886* (2018.01)

(52) U.S. Cl.
CPC ...... *C12Q 1/6886* (2013.01); *C12Q 2600/112* (2013.01); *C12Q 2600/118* (2013.01); *C12Q 2600/158* (2013.01); *C12Q 2600/16* (2013.01); *G01N 2800/52* (2013.01)

(58) Field of Classification Search
None
See application file for complete search history.

(56) References Cited

U.S. PATENT DOCUMENTS 6,582,908 B2 * 6/2003 Fodor ............... B01J 19/0046
435/288.3
7,517,952 B1 4/2009 Xu et al.
2011/0136683 A1 * 6/2011 Davicioni ............ C12Q 1/6886
506/7
2012/0039889 A1 2/2012 Rubin et al.
2013/0023434 A1 * 1/2013 Van Laar ............... G06F 19/24
506/9

FOREIGN PATENT DOCUMENTS

WO 2010/006048 A2 1/2010
WO 2011/153287 A2 12/2011

OTHER PUBLICATIONS

Haynes et al Electrophoresis. 1998. 19: 1862-1871.*
Gokmen-Polar et al. Cancer Research. 2001. 61: 1375-1381.*
Epstein, J. healthline. Lactate Dehydrogenase Test, May 26, 2017, available via url: < healthline.com/health/lactate-dehydrogenase-test#test4>, pp. 1-5, printed on Sep. 18, 2017.*
WebMD "Lactic Acid Dehydrogenase (LDH)" available via url: <webmd.com/a-to-z-guides/lactic-acid-dehydrogenase-ldh>, printed on Sep. 18, 2017.*
Murashita K, et al; "Ghrelin, Cholecystokinin, and Peptide YY in Atlantic Salmon (*Salmo salar*); Molecular Cloning and Tissue Expression," General and Comparative Endocrinology, Dec. 6, 2008, pp. 223-235,vol. 160.
Helo P, et al; "Circulating Prostate Tumor Cells Detected by Reverse Trancription—PCR in Men with Localized or Castration-Refractory Prostate Cancer: Concordance with CellSearch Assay and Association with Bone Metastases and with Survival," Clinical Chemistry, 2009, pp. 765-773, vol. 55, No. 4.
Vogelzang, MD, N.; "CellSearch Circulating Tumor Cell (CTC) Test Case Study," CellSearch, Circulating Tumor Cell Test, Veridex, LLC, 2008, p. 2.
International Search Report for PCT/US2013/055563 dated Jan. 3, 2014.
Edwards, S., et al., "Expression Analysis onto Microarrays of Randomly Selected cDNA Clones Highlights HOXB13 as a Marker of Human Prostate Cancer", *British Journal of Cancer*, vol. 92(2), pp. 376-381 (2005).

* cited by examiner

*Primary Examiner* — Carla J Myers
(74) *Attorney, Agent, or Firm* — Heslin Rothenberg Farley and Mesiti, PC; Kathy Smith Dias

(57) ABSTRACT

Using an RT-PCR platform, detection of gene transcripts highly expressed in prostate tissue and expressed in peripheral blood mononuclear cells (PBMC) from patients with mCRPC can provide a more reliable and robust prediction of poor overall survival than that of CTC enumeration in mCRPC. Disclosed is the identification of five genes, KLK3, KLK2, HOXB13, GHRL2 and FOXA1, the detection of two (2) or more transcripts of which predicts overall poor survival. The test is performed on blood samples that have been collected in collection tubes that stabilize intracellular RNA, require minimal on-site processing and can be easily stored and shipped for subsequent extraction of total RNA from whole blood for RT-PCR.

3 Claims, 6 Drawing Sheets

GENE EXPRESSION PROFILE ASSOCIATED WITH PROSTATE CANCER

CROSS-REFERENCE TO RELATED APPLICATIONS

This application is the U.S. National stage of PCT International Application No. PCT/US2013/055563 filed on Aug. 19, 2013 and published in English as WO 2014/028925 A1 on Feb. 20, 2014, which claims the priority of U.S. provisional application Ser. No. 61/684,351 filed Aug. 17, 2012, the entire contents of these applications are hereby incorporated by reference.

GOVERNMENT RIGHTS STATEMENT

This invention was made with government support under grant No. CA092629 awarded by the National Institutes of Health and W81XWH-09-1-0307 awarded by the Army Medical Research and Material Command. The government has certain rights in the invention.

FIELD OF THE INVENTION

The present invention relates generally to prostate cancer and in particular to prognostic biomarkers for patients with metastatic castration-resistant prostate cancer (mCRPC).

BACKGROUND OF THE INVENTION

Prostate cancer is the second leading cause of cancer death in American men, behind only lung cancer. In 2012, it is estimated that about 241,740 new cases of prostate cancer will be diagnosed and about 28,170 men will die of prostate cancer. Treatment options currently available for prostate cancer patients include surgery, radiation, hormonal therapy and chemotherapy. In addition, patients with castration-resistant prostate cancer with bone metastases are often treated with bisphosphonates to prevent skeletal-related events.

As a bone dominant disease, changes in prostate cancer metastases are difficult to assess using conventional imaging modalities, and only part of the treatment effect is reflected in serum prostate specific antigen (PSA) changes.

The need for molecular biomarkers predicting overall survival and monitoring treatment effects from a sample obtained repeatedly and with little inconvenience to the patient has recently focused on the technological advances in circulating tumor cell (CTC) detection, isolation, and capture. First described in 1869, CTC may be obtained from phlebotomy samples in a routine clinical practice setting. Initial studies of CTC in prostate cancer focused on detection of tumor cells using a reverse-transcription polymerase chain reaction (RT-PCR) based assay for the messenger RNA (mRNA) for PSA, also called kallikrein-related peptidase 3 (KLK3), in the mononuclear cell fraction of the blood that are presumed to be from CTC. To improve RT-PCR detection in peripheral blood, additional genes, highly expressed in tumor tissue and not expressed in peripheral blood nucleated cells (PBMC), have been studied as biomarkers to detect minimal residual or recurrent disease, such as prostate-specific membrane antigen, or markers of epithelial mesenchymal transition, or stem-cell origin. Depending on the sensitivity or specificity of the determinant being assayed, RT-PCR based detection rates range widely with disease extent in patients with castration resistant metastatic disease (CRPC). The wide range of results reflects the lack of standardization in sample processing and the analytical methods used for detection and in heterogeneous patient selection. Of particular interest, an early study using an RT-PCR based detection approach was the finding that PSA mRNA could be detected in patients who had no detectable serum PSA while responding clinically to androgen depletion therapy. This suggested that the continued detection of tumor cells in blood would provide unique clinical information relative to PSA because it represents an intrinsic property of the tumor that is independent of the level of androgens in the blood.

Before the role of any assay or device in medical decision-making can be determined, it is essential that it meet rigorous performance requirements. In particular, it is essential that the assay be "fit for the purpose" or "analytically valid" prior to evaluating the association of the biomarker(s) reported from using the assay with clinical outcomes. For the assay of CTC, it was not until the CellSearch assay was cleared by the Food and Drug Administration (FDA),[19] that more extensive clinical CTC testing became feasible. With this assay, detection rates are highest in patients with advanced disease, and those who have progressed in multiple therapies. It followed that survival times varied inversely with baseline CTC number as a continuous variable, but survival times for patient with low counts ranged from very short to very long. The clinical utility of monitoring CTC changes with treatment as an efficacy-response surrogate biomarker of survival is currently being tested in large phase III trials.

A limitation of the assay was the failure to detect cells in a significant proportion of patients with CRPC for whom specific therapeutic approaches are being developed, particularly the pre-chemotherapy space, highlighting the need to develop assays that detect cells in more patients at a higher frequency.

Thus, there is a critical unmet need in prostate cancer drug development and treatment for outcome measures that reflect clinical benefit.

SUMMARY OF THE INVENTION

Here is disclosed the development and analytical validation of an RT-PCR platform to detect gene transcripts highly expressed in prostate tissue and expressed in peripheral blood mononuclear cells (PBMC) from patients with mCRPC. The test is performed on blood samples that have been collected in special collection tubes that stabilize intracellular RNA, require minimal on-site processing and can be easily stored and shipped for subsequent extraction of total RNA from whole blood for RT-PCR. Detecting two (2) or more transcripts of five genes can provide a more reliable and robust prediction of poor overall survival than that of CTC enumeration in mCRPC.

In one aspect, the invention relates to a method of predicting overall survival of a prostate cancer patient, the method comprising: (a) analyzing a blood sample from the patient for the presence or absence of an expression product of each of genes KLK3, KLK2, HOXB13, GHRL2 and FOXA1 in the blood sample; and (b) predicting poor overall (median) survival when an expression product from two or more of the tested genes is detected in the patient sample.

In a closely related aspect, the invention relates to a method of predicting overall survival of a prostate cancer patient, the method comprising: (a) analyzing a blood sample from the patient for the presence or absence of an expression product of each of genes KLK3, KLK2, HOXB13, GHRL2 and FOXA1; and (b) predicting overall (median) survival of about 15 to 18 months when an expression product from one of the tested genes is detected in the patient sample and overall (median) survival of about 11 to 15 months when an expression product from two or more tested genes is detected in the patient sample. The absence of expression products of any of the tested genes is predictive of overall (median) survival of about 36 to 42 months. Expression products such as RNA transcripts or cDNAs are detected using real time PCR. The present method is useful in predicting overall survival in patients with metastatic castrate-resistant prostate cancer (mCRPC).

In a related aspect, the invention relates to a method for predicting overall survival in a prostate cancer patient, the method comprising: (a) contacting genetic material obtained from a blood sample from the patient with a plurality of oligonucleotide primers, wherein said plurality comprises at least one pair of oligonucleotide primers for each of genes KLK3, KLK2, HOXB13, GHRL2 and FOXA1; (b) performing PCR on said sample; (c) determining the presence or absence of an expression product of each of KLK3, KLK2, HOXB13, GHRL2 and FOXA1 in said blood sample from the patient; and (d) predicting (i) overall (median) survival of about 15 to 18 months when an expression product from one tested genes is detected in the patient sample; (ii) overall (median) survival of about 11 to 15 months when an expression product from two tested genes is detected in the patient sample; or (iii) overall (median) survival of about 36 to 42 months when no expression products of any of the tested genes is detected in the patient sample.

In yet another related aspect, the invention relates to a kit and/or primer set consisting essentially of PCR primers and probes for the detection of gene products of genes KLK3, KLK2, HOXB13, GHRL2 and FOXA1. In one embodiment, the kit or primer set of the invention includes oligonucleotides complementary to transcripts of each of genes KLK3, KLK2, HOXB13, GHRL2 and FOXA1. A kit of the invention may optionally include containers for blood collection that are designed to stabilize intracellular RNA prior to extraction.

DETAILED DESCRIPTION OF THE INVENTION

Figure 1:
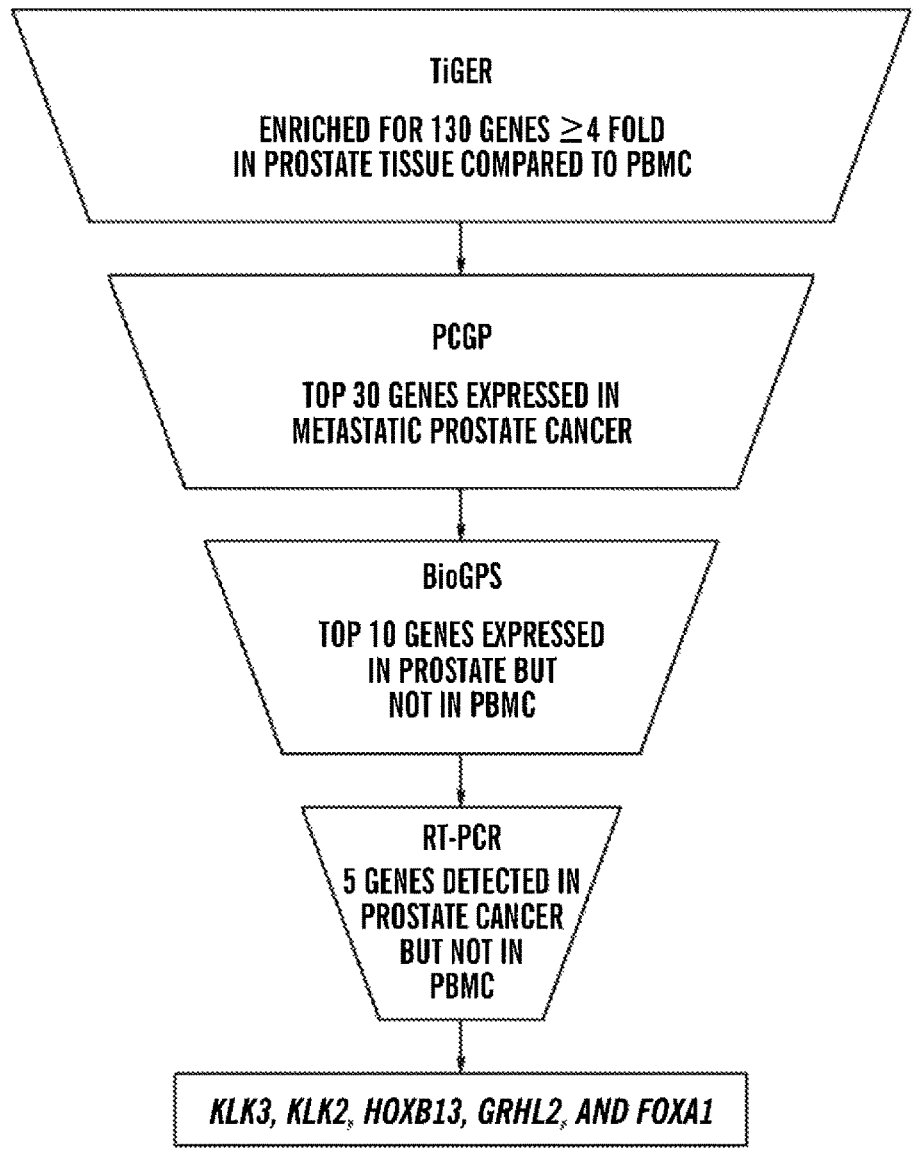
FIG. 1 is a schematic of the selection of a panel of prostate specific genes that are highly expressed in prostate but not expressed in peripheral blood mononuclear cells (PBMC). Tissue-specific Gene Expression and Regulation (TiGER), Prostate Cancer Genomic Project, and Novartis Gene Expression Database were queried for genes expressed in prostate tissue, but not expressed in PBMC, using Bio-GPS.
Figure 2:
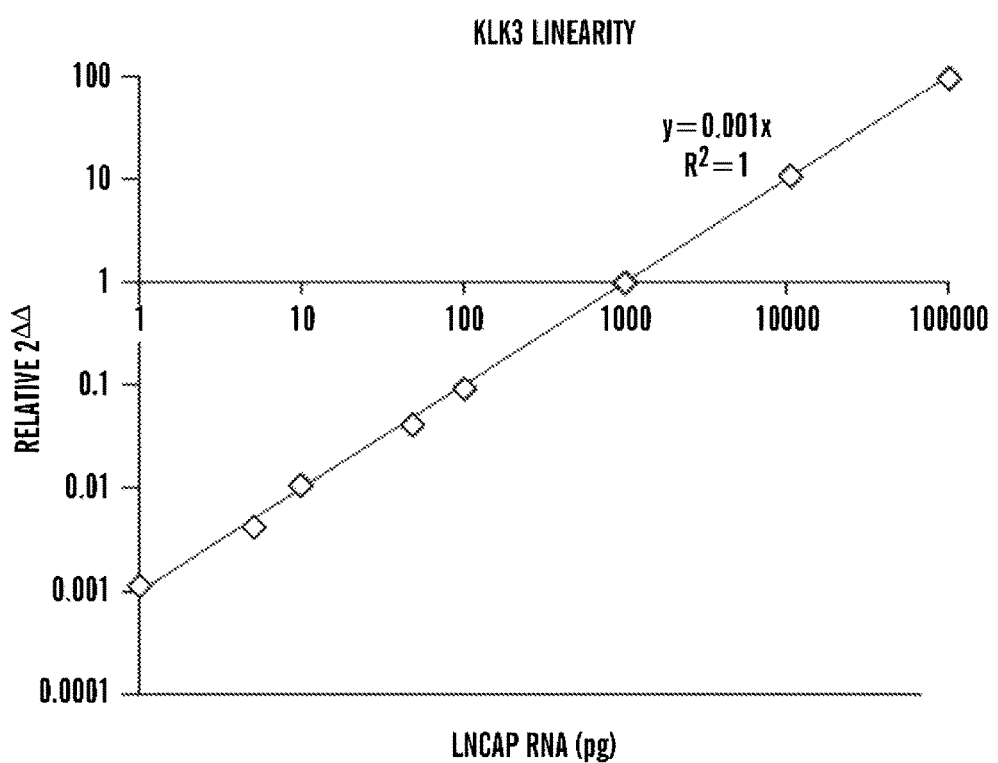
FIG. 2 is a graph showing the analytical validation of the RT-PCR assay for KLK3. The dynamic linearity range and the limit of detection were established based on LNCaP dilutions from 1 pg to 100 ng. Detection thresholds for each gene were chosen by ROC analysis of an independent set of 56 mCRPC patients versus 51 healthy volunteers, and results were reported as transcripts present or absent (ROC curves).

All publications, patents and other references cited herein are hereby incorporated by reference in their entirety into the present disclosure.

In practicing the present invention, many conventional techniques in molecular biology are used, which are within the skill of the ordinary artisan. Some techniques are described in greater detail in, for example, Molecular Cloning: a Laboratory Manual 3rd edition, J. F. Sambrook and D. W. Russell, ed. Cold Spring Harbor Laboratory Press 2001, the contents of this and other references containing standard protocols, widely known to and relied upon by those of skill in the art, including manufacturers' instructions are hereby incorporated by reference as part of the present disclosure.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

Abbreviations used herein:
mCRPC: metastatic castrate-resistant prostate cancer
CTC: circulating tumor cell
Lactase dehydrogenase: LDH
PBMC: peripheral blood mononuclear cells The term "overall survival" as that term is known in the art refers to time in months or years from surgery to death from any cause.

The term "primer" as that term is known in the art refers to an oligonucleotide that is complementary to a particular nucleic acid sequence of a template and is capable of acting as a point of initiation of extension with a polymerase under suitable PCR conditions and when used in suitable PCR primer pairs, will produce an amplicon of the target. The primer is preferably single stranded but can also be double stranded. If double stranded, the primer is first treated to separate its strands before being used to prepare extension products. Preferably, the primer is an oligodeoxyribonucleotide. The exact number of nucleotides in the primers will depend on many factors, including temperature, source of primer and the use of the method. The PCR primers of the present invention generally have about 18 to 25 nucleotides but can contain more or less. Methods for the design and synthesis of PCR primers are readily known in the art.

The terms "predict," "predictive" and "prediction" refer to the likelihood that a patient will have a particular clinical outcome, whether positive or negative, following surgical removal of the primary tumor. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen. The prediction may include prognostic factors.

The term "probe" refers to a single-stranded nucleic acid molecule that can base pair with a complementary single stranded target nucleic acid to form a double-stranded molecule. As the term is known in the art, the term "oligonucleotide" refers to a nucleic acid, generally of at least 18 nucleotides, that is hybridizable to a genomic DNA molecule, a cDNA molecule, a plasmid DNA or an mRNA molecule. Labeled oligonucleotides can be used as probes to detect the presence of a nucleic acid.

In order to improve the frequency of informative biomarker detection in patients with CRPC from the current rates with the FDA-cleared CTC enumeration CellSearch method, a highly sensitive RT-PCR assay for prostate specific-transcripts in whole blood was developed. This assay was first analytically validated for robust performance in samples from patients with CROP in a CLIA certified laboratory, according to the FDA Critical Path.[18] In addition to higher detection rates and relative ease of use compared to the CellSearch method, and the prognostic value as a biomarker of overall survival, assaying for 2 or more prostate specific-transcript detection in whole blood provides a potential informative tool for androgen-driven pathway functionality as a predictive biomarker for sensitivity to androgen receptor (AR)-targeted therapies.

Sensitive assays have been long utilized to detect low levels of expression of cancer specific genes in the mononuclear cell fraction of the blood presumed to be from CTC. In some cases, the tumor specific mRNA represents phagocytosed tumor cells in macrophages, and does not represent intact tumor cells. Messenger RNA for prostate specific has been studied in the peripheral blood of patients with prostatic cancer, and the frequency of detection of prostate specific transcripts is correlated with tumor stage. Additional markers are under investigation for detection of CTC from patients with colorectal, breast, lung and head and neck cancers, and these PCR-based assays have been also tested as biomarkers of prognosis and response-indicators. Serial monitoring by RT-PCR of a multimarker panel for melanoma during biochemotherapy may be useful for predicting therapeutic efficacy and disease outcome, although additional studies are necessary.

Clinical qualification follows a strict evidentiary process linking the biomarker with biological processes and clinical endpoints specific for the context of use that the test result will be used to inform. Analogous to our approach with the evaluation of drugs, our biomarker studies are conducted in defined patient populations using strict eligibility criteria under Institutional Review Boards approved protocols with patient informed consent. Testing a biomarker clinic requires robust assays for the biomarker that give consistent and reproducible results, a process termed analytical validation and outlined in the FDA Critical Path. Components of the validation process include sensitivity, specificity, false positive and false negatives, and positive and negative predictive values in relation to established standards if any. Once the analytical performance of an assay has been established, clinical testing can begin. Whether the assay in question needs full CLIA certification before clinical testing is controversial, but is a regulatory requirement for qualification.

Establishing the role of a diagnostic test in medical decision-making is not straightforward. The first consideration is the context of use for which the test is intended. For RT-PCR based assays, the situation is complicated by the broad range of assays and devices currently in use and under development. Underappreciated is that different assays, be they for enumeration or biologic profiling, may not be evaluating the same cells or the same determinant in cells, and as such are reporting different biomarkers. Underestimated is the complexity of establishing the analytical validity of an assay so that it can be used in rigorous series of trials needed to establish the role of the test in the clinic. Problematic as well is the paucity of dedicated trials designed specifically to address biomarker questions. The result is a literature that is replete with reports describing "significant results," whose clinical significance has not yet been established. More significant power to discriminate between low and high risk of a specific outcome could be obtained by combining multiple biomarkers, such as serum based LDH, albumin, serum PSA, with CellSearch CTC and prostate specific-transcript detection, which will ultimately result in a "basket" biomarker meant to influence medical decision-making.

The present disclosure describes the development and analytical validation of a sensitive RT-PCR-based assay to detect prostate specific transcripts in whole blood from men with CROP, and explores the relationship between prostate-specific mRNA detection and clinical outcome of treated patients.

Quantitative Real-Time PCR (QRT-PCR)

Real-time PCR is able to detect sequence-specific PCR products as they accumulate in "real-time" during the PCR amplification process. QRT-PCR may be used to measure the expression of a plurality of biomarkers. In QRT-PCR, the RNA template is generally reverse transcribed into cDNA, which is then amplified via a PCR reaction. The amount of PCR product is followed cycle-by-cycle in real time, which allows for determination of the initial concentrations of mRNA. To measure the amount of PCR product, the reaction may be performed in the presence of a fluorescent dye, such as SYBR Green, which binds to double-stranded DNA. The reaction may also be performed with a fluorescent reporter probe that is specific for the DNA being amplified. A non-limiting example of a fluorescent reporter probe is a TaqMan™ probe (Applied Biosystems, Foster City, Calif.). The fluorescent reporter probe fluoresces when the quencher is removed during the PCR extension cycle. Muliplex QRT-PCR may be performed by using multiple gene-specific reporter probes, each of which contains a different fluorophore. Fluorescence values are recorded during each cycle and represent the amount of product amplified to that point in the amplification reaction. To minimize errors and reduce any sample-to-sample variation, QRT-PCR is typically performed using a reference standard. The ideal reference standard is expressed at a constant level among different tissues, and is unaffected by the experimental treatment. The level of mRNA in the original sample may be determined using calculations well known in the art.

In one embodiment of the present invention, real time PCR is used to detect expression products, for example mRNA transcripts, in a blood sample from a mCRPC patient of a panel of genes, KLK3, KLK2, HOXB13, GHRL2 and FOXA1 that are predictive of overall survival. In one embodiment, blood is collected into tubes, for example PAXgene Blood RNA tubes (Qiagen), which are specially designed for integrated collection, and stabilization of RNA by protecting it from degradation by RNases. Using either manual or automated procedures, RNA is extracted from the blood using known methods. Briefly, purification begins by centrifugation of the sample to pellet nucleic acids in the tube. The pellet is washed and resuspended, followed by manual or automated RNA purification using gene-specific primers and probes.

Once the RNA is purified, expression of genes of the five gene panel, KLK3, KLK2, HOXB13, GHRL2 and FOXA1 is determined using real time PCR in accordance with methods known in the art. At least one set of primers/probes specific for each of the five genes is used; in some embodiments, primers and probes for a reference standard. One of skill in the art will recognize that in some instances, the determination of the expression of stable "housekeeping genes" may be desirable as a means for normalizing RNA expression in real-time PCR. The appropriate housekeeping genes will be known to those of skill in the art.

Detection of transcripts of any two of the five genes is predictive of a poor outcome, i.e., overall survival of about 11 to 14 months. If a gene product of one of the genes is present, overall survival is predicted to be about 15 to 18 months. Overall survival of about 36 to 42 months is likely when no transcripts for any of the genes are detected in the blood of the patient.

Kits

A further aspect of the invention provides kits for predicting survival or prognosis of a subject with prostate cancer. A kit of the invention typically comprises a plurality of agents for measuring the expression of a plurality of genetic biomarkers including, for example, an array of polynucleotides complementary to the mRNAs of the biomarkers. In one embodiment, the agents in the kit for measuring biomarker expression may comprise a plurality of PCR probes and/or primers for QRT-PCR.

The following examples are provided in order to demonstrate and further illustrate certain embodiments and aspects of the present invention and are not intended to be construed as limiting the scope thereof.

EXAMPLES

Patients and Healthy Volunteers

To select prostate cancer enriched gene transcripts for detection by RT-PCR, the Tissue-specific Gene Expression and Regulation (TiGER) database, the Prostate Cancer Genomic Project (15), and the Novartis Gene Expression Database (16) were interrogated for genes that were overexpressed inprostate tissue relative to peripheral blood mononuclear cells (PBMC). The 130-gene set, 30-gene set and 10-gene set are shown below in Tables 6, 7 and 8, respectively.

Patients included in the training and validation sets were men treated at MSKCC between August 2006 and February 2009 for progressive mCRPC, according to PSA Working Group 2 criteria. Control samples were obtained from healthy volunteers with no evidence of prostate cancer. Signed informed consent was obtained based on Institutional Review Board-approved protocols prior to acquiring any samples that were clinically annotated and anonymized before batching for testing.

CTC were enumerated from 7.5 mL of blood collected in CellSave tubes (Veridex, Raritan, N.J.) using the FDA-cleared CellSearch system (Veridex), as previously described.

Protocol for Sample Collection, Processing and Analysis for RT-PCR in Whole Blood The analytical validation of prostate specific transcript RT-PCR assays and clinical sample testing were performed according to CLIA regulatory guidelines in the Clinical Chemistry laboratory at MSKCC.

Sample collection: 2.5 mL peripheral blood was collected in PAXgene Blood RNA tubes (QIAGEN, Valencia, Calif.) from patients and healthy volunteers, according to manufacturer's instructions. Samples were incubated at room temperature for 24 h and stored at −80° C. until batch processing. Stability of blood in CellSave tubes for CellSearch assay was established previously to up to 96 hr, and gene transcript levels remain stable in PAXgene Blood RNA tubes for more than 50 months at −70° C. (PreAnalytiX). Human LNCaP prostate cancer cell line was purchased from American Type Culture Collection (Manassas, Va.).

Sample processing for analysis: Total RNA was extracted using PAXgene Blood RNA Kit (QIAGEN) for blood, and QIAGEN RNeasy Kit for cell lines, according to manufacturer's instructions. DNase I digestion was carried out to remove genomic contamination. RNA Integrity Number (RIN) of ≥6 was used to demonstrate satisfactory RNA quality using Agilent RNA Nano Assay.

Primer-directed reverse transcription and real-time PCR for the panel of prostate specific transcripts was performed using 1.5 ul (~2%) of total RNA using the CellDirect One Step (Invitrogen) method, followed by 14 cycles of PCR. The amplified cDNA was used in a multiplex real time PCR preformed onto 48×48 dynamic array chip (Fluidigm, South San Francisco, Calif.) for 40 cycles, as previously described. The constant threshold (Ct) for each replicate was recorded. A replicate with no signal detected was attributed a value of 999.

Standard operating procedures developed and maintained at MSKCC were used for the analytical validation of the assays. Assay performance was tested for intra-assay coefficient of variation (CV) in 6 repeats in 3 independent experiments and inter-assay CV across six-log dilutions, each in triplicate by 3 different analysts. A CV % below 15% is accepted in Clinical Laboratory Improvement Amendments (CLIA)-certified laboratories for precision. The dynamic linearity of the assay was tested in 7-fold range of dilutions from 0.1 pg to 1,000 ng of LNCaP RNA. The linear correlation coefficient was calculated, and the concordance between a standard PCR platform (Eppendorf Realplex, Hauppauge, N.Y.) and the multiplex PCR assay was tested with five serial dilutions. Each patient's sample was run in 6 replicates of real time PCR. Each assay was tested individually, and in multiplex to exclude assay interference. The sensitivity of the assay was tested using LNCaP prostate cancer cells spiked at 10, 100, 500, and 1,000 cells per 2.5 mL of healthy volunteer blood in PAXgene tubes. Each patient sample was run in 6 replicates, and the mean Ct was calculated.

Interpretation of results: Receiver operator curves were used to establish detection thresholds for each gene by comparing the mean Ct of samples from CRPC patients in a training set versus healthy volunteers. Results were reported as transcripts present or absent, and the presence of two or more transcripts in each sample was considered as a positive PCR test.

Statistical methods: The frequency of PCR detection in blood from men with progressive mCRPC is described, and Kaplan-Meier method was used to estimate overall survival. To assess the discriminatory power of the baseline factors on survival, the factors were jointly entered into a proportional hazards model and the concordance probability estimate (CPE) was computed. The kappa measure of agreement between CTC and the gene panel is computed. PCR status by metastatic disease distribution was assessed using the Fisher's exact test.

Panel of Prostate Specific Transcript Detection by RT-PCR

The top10 genes expressed in prostate tissue and not expressed in PBMC, selected by analysis of available databases (FIG. 1) were NKX3.1, ACPP, NPY, HOXB13, GRHL2, FOXA1, SLC45A3, THRAP6, KLK2, and KLK3. Of these, KLK3, KLK2, HOXB13, GHRL2 and FOXA1 were selected because they did not show expression by RT-PCR in PBMC from healthy volunteers.

Patient Data

The clinical characteristics of 57 patients in the training set and the 97 patients in the validation set are detailed in Table 1. The patients with progressive mCRPC studied in the validation group had a median survival time of 17 month (95% CI 13.8, 23.5). All analyses are based on 87 of the 97 patients with complete marker information in the validation set.

TABLE 1

Baseline patient clinical characteristics.

| Characteristic | Training cohort No. (%) or median (range) (n = 56) | Validation cohort No. (%) or median (range) (n = 97) |
|---|---|---|
| Age, years | 73 (49-89) | 70 (47-90) |
| KPS | 80 (70-90) | 80 (70-90) |
| Chemistry | | |
| PSA, ng/ml | 171 (4.95-4865) | 67.51 (0.05-3096.37) |
| Hgb, g/dl | 12 (8.4-14.8) | 12.1 (9.2-15.4) |
| ALK, unit/L | 135 (39-2323) | 102 (31-1818) |
| LBH, unit/L | 258 (115-1352) | 204 (87-845) |
| ALB, g/dl | 4 (3.3-4.8) | 4.3 (3.4-5) |
| Primary treatment | | |
| Surgery | 22 (39%) | 43 (44%) |
| Radiation | 22 (39%) | 27 (28%) |
| No primary therapy | 12 (22%) | 27 (28%) |
| Systemic treatment | | |

TABLE 1-continued

Baseline patient clinical characteristics.

| | Training cohort No. (%) or median (range) (n = 56) | Validation cohort No. (%) or median (range) (n = 97) |
|---|---|---|
| Hormone therapy | | |
| 1-2 lines | 25 (45%) | 44 (45%) |
| 3 lines | 15 (27%) | 29 (30%) |
| ≥4 lines | 16 (28%) | 24 (25%) |
| Ketoconazole | 23 (41%) | 44 (45%) |
| Prior chemotherapy | | |
| None | 42 (75%) | 53 (55%) |
| Any | 14 (25%) | 44 (45%) |
| Site of metastatic disease | | |
| Bone | 51 (91%) | 88 (91%) |
| Lymph node | 30 (54%) | 49 (51%) |
| Liver | 7 (12%) | 13 (13%) |
| Lung | 1 (2%) | 13 (13%) |
| Other soft tissue | 4 (7%) | 3 (3%) |
| Deceased | 44 (79%) | 77 (79%) |
| Follow-up (months) | 34 (1-142) | 43.3 (6.8-154) |

Analytical Validation of Prostate Specific Transcript Detection in Blood

Standard procedures for specimen collection and handling: Blood samples were collected prior to drug administration, first in CellSave tubes and second in PAXgene tubes. Samples were delivered and processed in the Clinical Chemistry Laboratory.

Multiplex RT-PCR assay performance characteristics: Assay performance was tested for the multiplex detection of KLK3, KLK2, HOXB13, GRHL2, and FOXA1 using LNCaP RNA for intra- and inter-assay coefficient of variation (CV), dynamic linear correlation and established a reportable range. Robust intra- and inter-assay CV, dynamic linear correlation and reportable range of the multiplex detection panel are presented in Table 2. The recovery in RNA extraction and RT-PCR analysis of each gene transcript from 10 LNCaP cells spiked in 2.5 mL of healthy volunteer blood demonstrated <6% CV. ROC analysis of 51 healthy controls vs 56 CRPC patients in the training set established $C_t$ thresholds for KLK3, KLK2, GHRL2 and FOXA1 at 999 and HOXB13 at 837.3.

TABLE 2

Analytical validation of RT-PCR assay in CLIA-certified laboratory.

| | Assay CV | | | | | | Detectable signal (%) | |
|---|---|---|---|---|---|---|---|---|
| | Intra- (n = 18) | Inter- (n = 42) | Linear Correlation | Reportable Range | p-value | $C_t$ Threshold | Controls (n = 51) | Patients (n = 97) |
| KLK3 | 1.05% | 2.13% | 1 | 1 pg-100 ng | <0.001 | 26.9 | 0% | 55% |
| KLK2 | 0.27%* | 2.98% | 0.999 | 5 pg-100 ng | <0.001 | 40 | 0% | 39% |
| HOXB13 | 1.02% | 1.29% | 1 | 5 pg-100 ng | <0.001 | 34.4 | 6% | 53% |
| GRHL2 | 0.98% | 1.08% | 1 | 10 pg-100 ng | <0.001 | 40 | 0% | 29% |
| FOXA1 | 0.88% | 1.26% | 0.999 | 50 pg-100 ng | <0.001 | 40 | 0% | 42% |

Data reporting: The status of the multiplex prostate specific RT-PCR assay was reported as positive if two or more transcripts were detected and as negative if one or less transcripts were detected.

Detection of prostate specific transcripts in whole blood by RT-PCR: Total RNA yielded from PAXgene preserved blood samples correlated poorly with CTC counts (Pearson r=0.15) due to the variable peripheral blood mononuclear cells number. All CRPC patients' samples passed the RIN quality control.

Prostate specific transcripts for KLK3, KLK2, HOXB13, GHRL2 and FOXA1 were detected in 44 (51%), 34 (39%), 46 (53%), 26 (30%) and 41 (47%) of patients, respectively. Two or more genes were detected in 41/87 patients (47%, 95% CI 36-58%) of patients. Baseline unfavorable CTC (counts ≥5) were detected in 45 patients (46%, 95% CI 37-56%) in this cohort of patients. As described in Table 2, 40/45 CRPC-patients with ≥5 CTC and 13/52 CRPC patients with <5 CTC had 2 or more transcripts present in blood.

A separate analysis was performed to show the CPE after removing an individual gene. As shown, excluding one gene from the panel at a time had a minimal effect on discriminatory power of the survival estimate.

| Gene removed | CPE |
| --- | --- |
| HOXB13 | 0.750 |
| GRHL | 0.746 |
| FOXA1 | 0.748 |
| KLK2 | 0.749 |
| KLK3 | 0.751 |

Notably, 13 of the 52 patients (25%, 95% CI 16-38%) with CTC count of 4 or less had detectable 2 or more transcripts in blood, which could be explained by the CellSearch rigorous criteria in defining CTC as intact nucleated cytokeratin-positive and CD45-negative cells, whereas additional EpCAM-positive events are often found in the analysis chamber.

Figure 3:
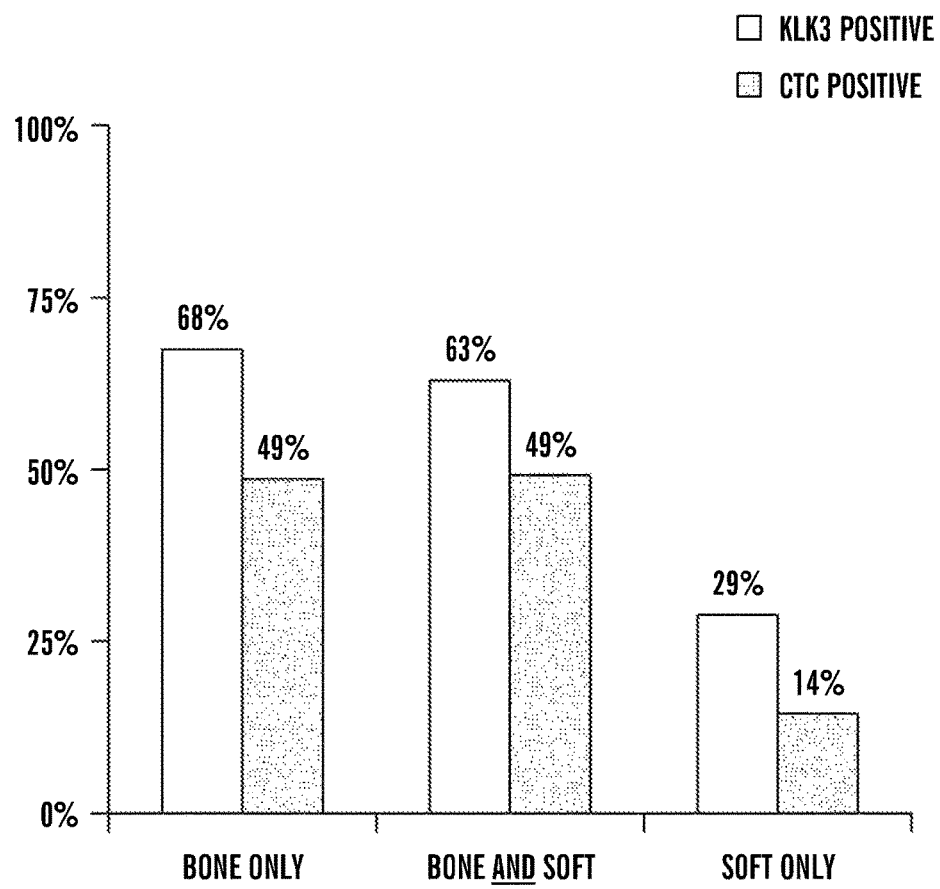
FIG. 3 is a graph showing the results of CTC enumeration (Cell Search) vs. detection of 2 or more prostate specific transcripts in whole blood. CTC count, 2 or more prostate specific transcript detection status among mCRPC patients with metastasis exclusively in bone (n=37), in bone and soft tissue (n=51) and soft tissue only (n=7).

Associations with disease distribution: Prostate specific 2 or more transcripts were more likely to be detected in patients with bone metastasis alone or bone and soft tissue involvement, relative to those with soft tissue only disease (FIG. 3). As expected, higher CTC numbers were found in patients with bone metastasis compared to soft tissue metastasis only. The frequency of detection of prostate specific transcripts was higher in each pattern of metastatic distribution group.

Prognostic value of detecting prostate specific transcripts in blood samples from patients with CRPC: Similar to CTC enumeration, transcript detection predicted overall survival in proportional hazards models that included LDH dichotomized at 250 (Table 3).

TABLE 3

Table 3. Correlation between prostate specific transcript detection (favorable: 0 or 1 prostate-specific transcript detected versus unfavorable: ≥2 transcripts detected) and CTC enumeration (favorable: ≤4 cells or unfavorable: ≥5 cells) based on prior chemotherapy exposure.

| | | Chemotherapy-naïve patients N = 53 (%) | Chemotherapy exposed patients N = 44 (%) |
| --- | --- | --- | --- |
| Transcript detected | 0 | 21 (40%) | 7 (16%) |
| | 1 | 9 (17%) | 9 (20%) |
| | 2 or more | 23 (43%) | 28 (64%) |
| CTC | Favorable | 35 (66%) | 17 (39%) |
| | Unfavorable | 18 (34%) | 27 (63%) |

Figure 4A:
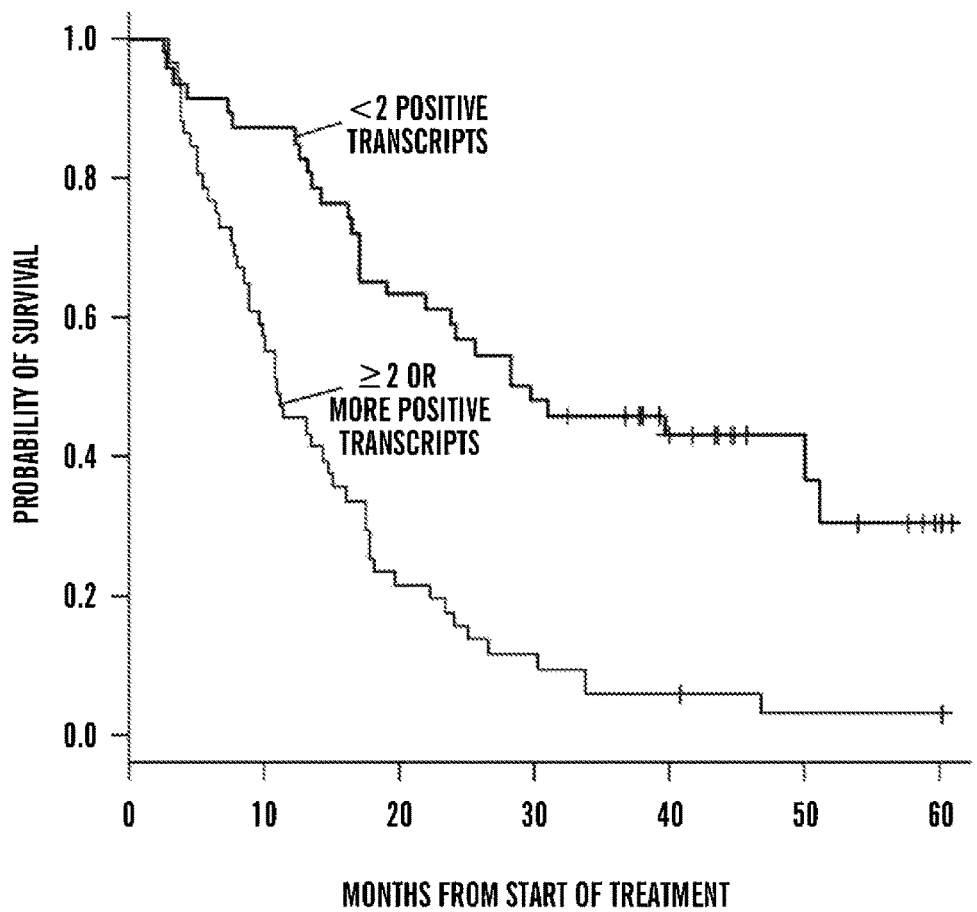
FIG. 4 is a Kaplan-Meier estimate of survival, calculated from time of blood draw, based on detection of 2 or more prostate specific transcripts (A) and baseline CTC counts (B).
Figure 4B:
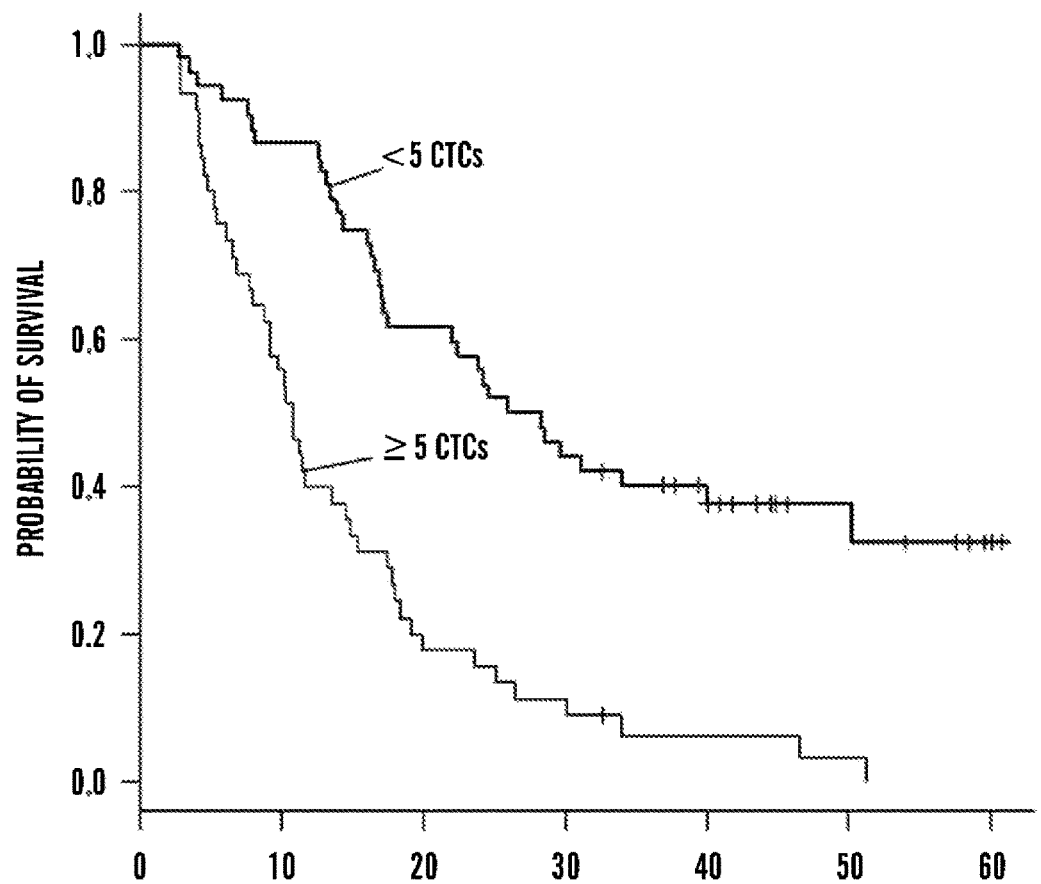

The predictive accuracy (CPE) of PCR detection+LDH was 0.785 (SE 0.036), comparable to CTC-enumeration+LDH (0.796, SE 0.035). In addition, using PCR detection of 2 or more transcripts, and LDH>250 as individual prognostic markers suggested an individual contribution of both in Kaplan-Meier analysis of survival for patients with CROP, as presented in FIG. 4.

TABLE 4

Table 4. The prognostic significance calculated based on A) CTC enumeration (favorable < 5 vs. unfavorable ≥ 5), or B) two or more prostate specific transcript detection in predicted overall survival in proportional hazards models that included LDH dichotomized at above and below 250. CPE, concordance probability estimate.

A

| Factor | Log Rel Risk | Se(log Rel Risk) | p-value |
| --- | --- | --- | --- |
| LDH ≥ 250 | 1.023 | 0.279 | <0.001 |
| CTC ≥ 5 | 1.000 | 0.271 | <0.001 |
| CPE = 0.771 (se 0.033) | | | |

TABLE 4-continued

Table 4. The prognostic significance calculated based on A) CTC enumeration (favorable < 5 vs. unfavorable ≥ 5), or B) two or more prostate specific transcript detection in predicted overall survival in proportional hazards models that included LDH dichotomized at above and below 250. CPE, concordance probability estimate.

CTC

| | <5 | ≥5 |
| --- | --- | --- |
| LDH 250 d | | |
| LDH < 250 | 36 | 25 |
| LDH > 250 | 5 | 21 |

B

| Factor | Log Rel Risk | Se (log Rel Risk) | p-value |
| --- | --- | --- | --- |
| LDH ≥ 250 | 0.912 | 0.285 | <0.001 |
| Any two genes low | 1.015 | 0.290 | <0.001 |
| CPE = 0.759 (se 0.035) | | | |

2 genes

| | Signal | No signal |
| --- | --- | --- |
| LDH 250 d | | |
| LDH < 250 | 36 | 25 |
| LDH > 250 | 5 | 21 |

Figure 5:
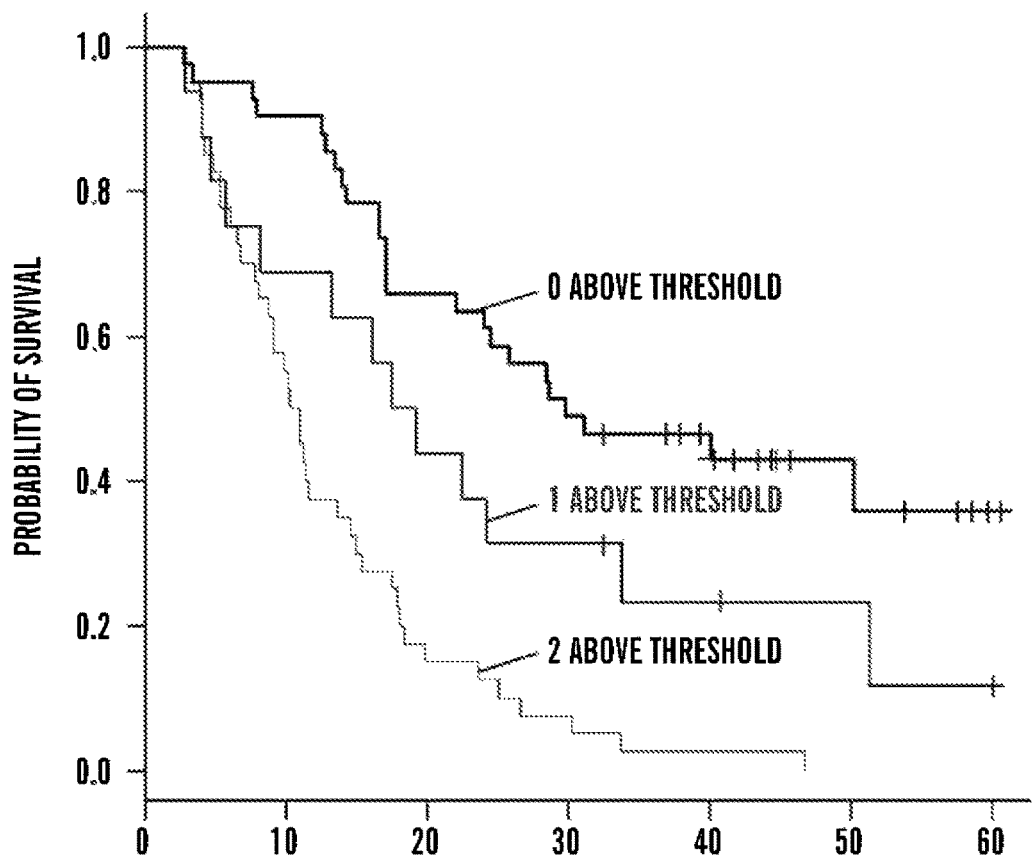
FIG. 5 is a Kaplan-Meier estimate of survival, calculated from time of blood draw, based on whether 0, 1 (positive gene signature or CTC), or 2 unfavorable risk factors (positive gene signature and CTC) were present.

Combined prognostic model: A model including both the gene panel and CellSearch results enabled a refinement of the risk assessment and in particular for patients with low (favorable) cell counts by Veridex, based on 0, 1, or 2 unfavorable risk factors as presented in Table 2. The CPE for this model is 0.752 (SE=0.038), indicating the model is a strong discriminator of patient risk. The Kaplan-Meier estimate of survival by number of unfavorable risk factors is depicted in FIG. 5. Patients with 0 unfavorable risk factors were in the best risk group, with a median survival of 29.8 months, while those with 1 or 2 unfavorable factors had estimated median survival of 18.4 months and 10.6 months, respectively.

Estimates of the hazard ratio from the Cox proportional hazards model based on CTC enumeration (favorable: ≤4 cells vs. unfavorable: ≥5 cells) and the 5-gene panel (favorable: ≤1 prostate-specific transcript detected vs. unfavorable: ≥2 transcripts detected). LCL, lower confidence limit, UCL, upper confidence limit.

TABLE 5

| Number of unfavorable risk factors | Number of patients | HR | 0.95 LCL | 0.95 UCL |
| --- | --- | --- | --- | --- |
| 0 | 41 | 1.00 | | |
| 1 | 16 | 1.88 | 0.96 | 3.70 |
| 2 | 40 | 4.34 | 2.55 | 7.40 |

TABLE 6

Distribution of the original 130 genes.

| Symbol | Enrichment factor (TiGER) |
| --- | --- |
| UPK3A | 25.5235 |
| SEMG1 | 24.1104 |
| PRAC | 23.9283 |
| SEMG2 | 23.6152 |
| MSMB | 23.2264 |
| EDC3 | 23.2264 |
| KLK2 | 22.7748 |

TABLE 6-continued

Distribution of the original 130 genes.

| Symbol | Enrichment factor (TiGER) |
|---|---|
| TGM4 | 21.6653 |
| KLK4 | 20.2061 |
| OR51E2 | 20.1094 |
| ACPP | 19.693 |
| TARP | 18.4554 |
| KLK3 | 18.3136 |
| NKX3-1 | 18.0329 |
| PPIL5 | 17.8664 |
| HOXB13 | 16.8346 |
| POTEG | 16.0703 |
| RLN1 | 15.3141 |
| PCDHB8 | 14.5848 |
| PCDHB13 | 14.5848 |
| SLC45A3 | 14.4948 |
| XCL2 | 13.9219 |
| FOXA1 | 13.629 |
| TRPM8 | 13.6125 |
| TMPRSS2 | 12.8894 |
| SRD5A2 | 12.7617 |
| PATE1 | 12.7617 |
| GLTSCR1 | 12.6767 |
| LOC150519 | 12.6488 |
| ATP5SL | 12.4288 |
| AR | 12.2513 |
| C5orf37 | 12.1727 |
| NWD1 | 12.0111 |
| ANO7 | 11.9641 |
| SLC39A2 | 11.7801 |
| TEPP | 11.6016 |
| DOCK9 | 11.2079 |
| MPHOSPH10 | 10.9386 |
| CYP24A1 | 10.9386 |
| TDRD6 | 10.7984 |
| ARHGAP6 | 10.7846 |
| FCER1A | 10.7467 |
| ZNF554 | 10.6348 |
| SPRR4 | 10.5097 |
| FLJ20184 | 10.4414 |
| C21orf84 | 10.2094 |
| CPNE4 | 10.176 |
| ALOX15B | 10.0092 |
| ZNF35 | 9.96039 |
| KCNJ5 | 9.9258 |
| C6orf141 | 9.81673 |
| PLA2G4F | 9.40339 |
| ACTG2 | 9.37597 |
| SULT2B1 | 9.32589 |
| LMAN1L | 9.21681 |
| C10orf125 | 9.00829 |
| CSTA | 8.84814 |
| SATB1 | 8.70801 |
| BMPR1B | 8.36114 |
| PAGE4 | 8.24605 |
| AMACR | 8.18935 |
| PTGFR | 8.12111 |
| EPC1 | 8.02543 |
| NEFH | 8.01319 |
| LPAR3 | 7.97609 |
| KCNC2 | 7.81331 |
| OR51E1 | 7.76802 |
| TTC8 | 7.7482 |
| SCGB3A1 | 7.65705 |
| CYP4F8 | 7.65705 |
| LOC643837 | 7.63523 |
| ZNF552 | 7.53152 |
| DNAJC19 | 7.52943 |
| PIP | 7.50691 |
| NPY | 7.38838 |
| WNT5B | 7.37345 |
| CD177 | 7.29242 |
| RPL22L1 | 7.25897 |
| TMEM220 | 7.14658 |
| MYH11 | 7.13156 |
| SLC2A12 | 7.04096 |
| TMEFF2 | 7.01195 |
| TTLL3 | 7.00997 |
| FOLH1 | 6.99838 |
| DNAH5 | 6.96095 |
| DNAH8 | 6.96095 |
| SCUBE2 | 6.93231 |
| RDH11 | 6.92832 |
| SLC14A1 | 6.83023 |
| ERGIC1 | 6.78767 |
| ZNP761 | 6.6583 |
| PSCA | 6.63611 |
| TSC22D2 | 6.55028 |
| IGF1 | 6.52926 |
| EMILIN2 | 6.52926 |
| EPHX2 | 6.51663 |
| PAEP | 6.49689 |
| NME4 | 6.4031 |
| S1PR5 | 6.38087 |
| OPLAH | 6.38087 |
| ITGA8 | 6.25065 |
| ZNF613 | 6.16084 |
| PART1 | 6.04504 |
| TNFRSF10D | 5.9251 |
| PDE9A | 5.91849 |
| SLC30A4 | 5.74278 |
| C1orf116 | 5.73784 |
| HOXA13 | 5.67189 |
| ABCC4 | 5.60563 |
| HIST1H4H | 5.60272 |
| DLK2 | 5.58326 |
| TRAPPC6B | 5.5257 |
| STEAP1 | 5.51859 |
| AQP2 | 5.51859 |
| PCP4 | 5.46932 |
| MST1R | 5.43943 |
| GRHL2 | 5.38569 |
| ZG16B | 5.37337 |
| FAM83A | 5.34213 |
| MARVELD2 | 5.23559 |
| CTSG | 5.22071 |
| AZGP1 | 5.19122 |
| PTGS2 | 5.18446 |
| LCAT | 5.16931 |
| RPL39 | 5.1047 |
| HOXD9 | 5.1047 |
| PSEN2 | 5.1047 |
| ING2 | 5.1047 |
| SLC26A7 | 5.1047 |
| SCGB1A1 | 5.02101 |

TABLE 7

Top 30 genes expressed in prostate cancer metastatic tissue (Prostate Cancer Genomic Project (13)

| Symbol | Enrichment factor (TiGER) | Mets (average) |
|---|---|---|
| OR51E2 | 20.1094 | 12.98 |
| KLK2 | 22.7748 | 12.08 |
| KLK3 | 18.3136 | 12.06 |
| LOC643837 | 7.63523 | 11.71 |
| IGF1 | 6.52926 | 11.3 |
| SLC30A4 | 5.74278 | 11.06 |
| SLC45A3 | 14.4948 | 10.96 |
| TMEM220 | 7.14658 | 10.77 |
| AMACR | 8.18935 | 10.74 |
| MARVELD2 | 5.23559 | 10.71 |
| ERGIC1 | 6.78767 | 10.63 |
| NKX3-1 | 18.0329 | 10.51 |
| FOXA1 | 13.629 | 10.41 |
| AR | 12.2513 | 10.38 |
| FOLH1 | 6.99838 | 10.34 |

TABLE 7-continued

Top 30 genes expressed in prostate cancer metastatic tissue (Prostate Cancer Genomic Project (13)

| Symbol | Enrichment factor (TiGER) | Mets (average) |
|---|---|---|
| RPL39 | 5.1047 | 10.29 |
| ZNF552 | 7.53152 | 10.17 |
| RDH11 | 6.92832 | 10 |
| ACPP | 19.693 | 9.98 |
| HOXB13 | 16.8346 | 9.94 |
| NME4 | 6.4031 | 9.94 |
| ABCC4 | 5.60563 | 9.81 |
| ZNF554 | 10.6348 | 9.69 |
| KLK4 | 20.2061 | 9.65 |
| NPY | 7.38838 | 9.65 |
| HIST1H4H | 5.60272 | 9.6 |
| KCNJ5 | 9.9258 | 9.55 |
| ZG16B | 5.37337 | 9.52 |
| GRHL2 | 5.38569 | 9.51 |
| TARP | 18.4554 | 9.46 |

TABLE 8

Top 10 genes expressed inprostate tissue but not in PBMC or in >2 tissues other than prostate tissue (Novartis Gene Expression Databse (14)).

| Symbol | Enrichment factor (TiGER) | Mets (average) | GNF tissues | RT-qPCR signal in PBMC | Final selection |
|---|---|---|---|---|---|
| KLK2 | 22.7748 | 12.08 | prostate only | NO | YES |
| KLK3 | 18.3136 | 12.06 | prostate only | NO | YES |
| SLC45A3 | 14.4948 | 10.96 | prostate only | YES | NO |
| NKX3-1 | 18.0329 | 10.51 | prostate, trachea | YES | NO |
| FOXA1 | 13.629 | 10.41 | prostate, lung, liver | NO | YES |
| AR | 12.2513 | 10.38 | prostate, liver, adipocytes | YES | NO |
| FOLH1 | 6.99838 | 10.34 | prostate only | YES | NO |
| ACPP | 19.693 | 9.98 | prostate only | YES | NO |
| HOXB13 | 16.8346 | 9.94 | prostate only | NO | YES |
| NPY | 7.38838 | 9.65 | prostate only | YES | NO |
| GRHL2 | 5.38569 | 9.51 | prostate, placenta | NO | YES |

REFERENCES

1. Ashworth T. A case of cancer in which cells similar to those in the tumours were seen in the blood after death. Aus Med J. 1869; 14:146-9
2. Ghossein R A, Scher H I, Gerald W L, et al. Detection of circulating tumor cells in patients with localized and metastatic prostatic carcinoma: clinical implications. J Clin Oncol. 1995; 13(5):1195-200. Epub May 1, 1995.
3. McShane L M, Hayes D F. Publication of tumor marker research results: the necessity for complete and transparent reporting. J Clin Oncol. 2012; 30(34):4223-32.
4. Zhang L, Wang C Y, Yang R, et al. Real-time quantitative RT-PCR assay of prostate-specific antigen and prostate-specific membrane antigen in peripheral blood for detection of prostate cancer micrometastasis. Urologic oncology. 2008; 26(6):634-40. Epub Mar. 3, 2008.
5. Danila D C, Anand A, Sung C C, et al. TMPRSS2-ERG status in circulating tumor cells as a predictive biomarker of sensitivity in castration-resistant prostate cancer patients treated with abiraterone acetate. Eur Urol. 2011; 60(5):897-904. Epub Aug. 2, 2011.
6. Pantel K, Brakenhoff R H, Brandt B. Detection, clinical relevance and specific biological properties of disseminating tumour cells. Nature reviews Cancer. 2008; 8(5): 329-40.
7. Danila D C, Fleisher M, Scher H I. Circulating tumor cells as biomarkers in prostate cancer. Clinical cancer research: an official journal of the American Association for Cancer Research. 2011; 17(12):3903-12. Epub Jun. 18, 2011.
8. Shaffer D R, Leversha M A, Danila D C, et al. Circulating tumor cell analysis in patients with progressive castration-resistant prostate cancer. Clinical cancer research: an official journal of the American Association for Cancer Research. 2007; 13(7):2023-9.
9. Danila D C, Heller G, Gignac G A, et al. Circulating tumor cell number and prognosis in progressive castration-resistant prostate cancer. Clinical cancer research: an official journal of the American Association for Cancer Research. 2007; 13(23):7053-8. Epub Dec. 7, 2007.
10. de Bono J S, Scher H I, Montgomery R B, et al. Circulating tumor cells predict survival benefit from treatment in metastatic castration-resistant prostate cancer. Clinical cancer research: an official journal of the American Association for Cancer Research. 2008; 14(19):6302-9. Epub Oct. 3, 2008.
11. Scher H I, Jia X, de Bono J S, et al. Circulating tumour cells as prognostic markers in progressive, castration-resistant prostate cancer: a reanalysis of IMMC38 trial data. Lancet Oncol. 2009; 10(3):233-9. Epub Feb. 14, 2009.
12. Scher H, Heller G, Molina A, et al. Evaluation of circulating tumor cell (CTC) enumeration as an efficacy response biomarker of overall survival (OS) in metastatic castration-resistant prostate cancer (mCRPC): Planned final analysis (FA) of COU-AA-301, a randomized double-blind, placebo-controlled phase III study of abiraterone acetate (AA) plus low-dose prednisone (P) post docetaxel. In: ASCO, editor: J Clin Oncol 29: 2011 (suppl; abstr LBA4517^); 2011.
13. Danila D C, Pantel K, Fleisher M, Scher H I. Circulating tumors cells as biomarkers: progress toward biomarker qualification. Cancer J. 2011; 17(6):438-50. Epub Dec. 14, 2011.
14. Liu X, Yu X, Zack D J, Zhu H, Qian J. TiGER: a database for tissue-specific gene expression and regulation. BMC Bioinformatics. 2008; 9:271. Epub Jun. 11, 2008.
15. Taylor B S, Schultz N, Hieronymus H, et al. Integrative genomic profiling of human prostate cancer. Cancer Cell. 2010; 18(1):11-22. Epub Jun. 29, 2010.
16. Su A I, Cooke M P, Ching K A, et al. Large-scale analysis of the human and mouse transcriptomes. Proc Natl Acad Sci USA. 2002; 99(7):4465-70. Epub Mar. 21, 2002.
17. Wu C, Orozco C, Boyer J, et al. BioGPS: an extensible and customizable portal for querying and organizing gene annotation resources. Genome Biol. 2009; 10(11):R130. Epub Nov. 19, 2009.
18. Scher H I, Eisenberger M, D'Amico A V, et al. Eligibility and outcomes reporting guidelines for clinical trials for patients in the state of a rising prostate-specific antigen: recommendations from the Prostate-Specific Antigen Working Group. J Clin Oncol. 2004; 22(3):537-56. Epub Jan. 31, 2004.
19. Allard W J, Matera J, Miller M C, et al. Tumor cells circulate in the peripheral blood of all major carcinomas but not in healthy subjects or patients with nonmalignant diseases. Clinical cancer research: an official journal of the American Association for Cancer Research. 2004; 10(20):6897-904.

20. Gonen M, Heller G. Concordance probability and discriminative power of proportional hazards regression. Biometrika. 2005; 92:965-70.
21. Lilja H, Ulmert D, Vickers A J. Prostate-specific antigen and prostate cancer: prediction, detection and monitoring. Nature reviews Cancer. 2008; 8(4):268-78.
22. Ewing C M, Ray A M, Lange E M, et al. Germline mutations in HOXB13 and prostate-cancer risk. N Engl J Med. 2012; 366(2):141-9.
23. Gerhardt J, Montani M, Wild P, et al. FOXA1 promotes tumor progression in prostate cancer and represents a novel hallmark of castration-resistant prostate cancer. Am J Pathol. 2012; 180(2):848-61.
24. Barbieri C E, Baca S C, Lawrence M S, et al. Exome sequencing identifies recurrent SPOP, FOXA1 and MED12 mutations in prostate cancer. Nature genetics. 2012; 44(6):685-9.
25. Grasso C S, Wu Y M, Robinson D R, et al. The mutational landscape of lethal castration-resistant prostate cancer. Nature. 2012; 487(7406):239-43.
26. Belikov S, Oberg C, Jaaskelainen T, Rahkama V, Palvimo J J, Wrange O. FoxA1 corrupts the antiandrogenic effect of bicalutamide but only weakly attenuates the effect of MDV3100 (Enzalutamide). Molecular and cellular endocrinology. 2012.
27. Kang X, Chen W, Kim R H, Kang M K, Park N H. Regulation of the hTERT promoter activity by MSH2, the hnRNPs K and D, and GRHL2 in human oral squamous cell carcinoma cells. Oncogene. 2009; 28(4):565-74.
28. FDA. Guidance for Industry. E16 Biomarkers Related to Drug or Biotechnology Product Development: Context, Structure, and Format of Qualification Submissions. August 2011.
29. Veridex. 510 k for CellSearch Veridex. 2008.

We claim:

1. A method of identifying overall survival of a metastatic castrate-resistant prostate cancer patient, the method comprising:
    (a) assaying a blood sample from the patient to detect the concentration of lactate dehydrogenase (LDH) in the blood sample, wherein the concentration of LDH detected is at least 250 U/liter;
    (b) contacting RNA from a stabilized blood sample from the patient with a set of oligonucleotide primers, wherein the set of oligonucleotide primers consists of at least one pair of oligonucleotide primers for each of genes KLK3, KLK2, HOXB13, GHRL2 and FOXA1;
    (c) performing PCR on said RNA to produce amplified RNA expression products;
    (d) detecting the presence of an amplified RNA expression product of any of KLK3, KLK2, HOXB13, GHRL2 and FOXA1 in the stabilized blood sample from the patient; and
    (e) identifying the patient as one who will have:
        (i) overall survival of about 15 to 18 months when an RNA expression product of one of KLK3, KLK2, HOXB13, GHRL2 and FOXA1 is detected in the patient's stabilized blood sample;
        (ii) overall survival of about 11 to 15 months when RNA expression products of two of KLK3, KLK2, HOXB13, GHRL2 and FOXA1 are detected in the patient's stabilized blood sample; or
        (iii) overall survival of about 36 to 42 months when no RNA expression products of any of KLK3, KLK2, HOXB13, GHRL2 and FOXA1 are detected in the patient's stabilized blood sample.

2. A method of predicting overall survival of a metastatic castrate-resistant prostate cancer patient, the method comprising:
    (a) assaying a blood sample from the patient to detect the concentration of lactate dehydrogenase (LDH) in the blood sample, wherein the concentration of LDH detected is at least 250 U/liter;
    (b) performing a nucleic acid detection assay on a stabilized blood sample from the patient to determine the quantity of RNA or cDNA expression products of the KLK3, KLK2, HOXB13, GHRL2 and FOXA1 genes in the stabilized blood sample; and
    (c) predicting:
        (i) overall survival of about 15 to 18 months when an RNA or cDNA expression product of one of KLK3, KLK2, HOXB13, GHRL2 and FOXA1 is detected in the patient sample;
        (ii) overall survival of about 11 to 15 months when an RNA or cDNA expression product of two of KLK3, KLK2, HOXB13, GHRL2 and FOXA1 are detected in the patient sample; or
        (iii) overall survival of about 36 to 42 months when no expression RNA or cDNA products of any of KLK3, KLK2, HOXB13, GHRL2 and FOXA1 are detected in the patient sample.

3. The method of claim 1, wherein said PCR comprises real time PCR.

* * * * *